(12) United States Patent
Mou et al.

(10) Patent No.: US 11,002,719 B2
(45) Date of Patent: May 11, 2021

(54) ACTUATING AND SENSING MODULE

(71) Applicant: Microjet Technology Co., Ltd., Hsinchu (TW)

(72) Inventors: Hao-Jan Mou, Hsinchu (TW); Shih-Chang Chen, Hsinchu (TW); Li-Pang Mo, Hsinchu (TW); Jia-Yu Liao, Hsinchu (TW); Hung-Hsin Liao, Hsinchu (TW); Chih-Feng Lin, Hsinchu (TW); Jheng-Wei Chen, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 443 days.

(21) Appl. No.: 16/042,602

(22) Filed: Jul. 23, 2018

(65) Prior Publication Data

US 2019/0064134 A1 Feb. 28, 2019

(30) Foreign Application Priority Data

Aug. 31, 2017 (TW) .................................. 106129650

(51) Int. Cl.
*G01N 33/00* (2006.01)
*F04B 43/04* (2006.01)
*F04B 45/047* (2006.01)
*G01N 29/22* (2006.01)

(52) U.S. Cl.
CPC ....... *G01N 33/0073* (2013.01); *F04B 45/047* (2013.01); *G01N 29/222* (2013.01);
(Continued)

(58) Field of Classification Search
USPC .................................. 73/31.01, 31.02, 31.06
See application file for complete search history.

(56) References Cited

U.S. PATENT DOCUMENTS 5,719,325 A * 2/1998 Kiesele ................ G01N 27/404
204/406
7,249,490 B2 * 7/2007 Pendergrass ....... G01N 33/0009
73/23.2
(Continued)

FOREIGN PATENT DOCUMENTS

CN 104235081 A 12/2014
CN 103411864 B 12/2015
(Continued)

OTHER PUBLICATIONS

Curiejet, "MicroJet Piezoelectric Micro Air Pump Datasheet," GS8S9, retrieved from URL:www.curiejet.com, Jan. 1, 2018, pp. 1-6.
(Continued)

*Primary Examiner* — Daniel S Larkin
(74) *Attorney, Agent, or Firm* — Birch, Stewart, Kolasch & Birch, LLP (57) ABSTRACT

An actuating and sensing module includes a first substrate, a second substrate, an actuating device and a sensor. A gas flow channel is formed by stacking the first substrate and the second substrate. The gas inlet, the gas flow channel and the gas outlet are in communication with each other to define a gas flow loop. The actuating device is disposed in the gas inlet of the second substrate and electrically connected to a control circuit to obtain a driving power. The sensor is disposed in the gas flow loop and electrically connected to a control circuit of the first substrate to transmit sensed data. While the actuating device drives outside gas from the outside, the gas is transported into the gas flow loop and sensed by the sensor.

18 Claims, 6 Drawing Sheets

(52) U.S. Cl.
CPC ....... *G01N 33/004* (2013.01); *G01N 33/0026* (2013.01); *G01N 33/0047* (2013.01)

(56) References Cited

U.S. PATENT DOCUMENTS

| | | | |
|---|---|---|---|
| 2006/0010974 A1* | 1/2006 | Koyano | G01N 33/0009 73/431 |
| 2010/0139389 A1* | 6/2010 | Morita | G01F 5/00 73/204.11 |
| 2015/0096352 A1* | 4/2015 | Peterson | H04L 12/282 73/31.02 |
| 2016/0103082 A1* | 4/2016 | Kimura | G01N 33/005 73/25.01 |
| 2016/0209436 A1 | 7/2016 | Wu et al. | |
| 2019/0154551 A1* | 5/2019 | Richter | G01N 1/2273 |

FOREIGN PATENT DOCUMENTS

| | | |
|---|---|---|
| CN | 105874333 A | 8/2016 |
| CN | 107014953 A | 8/2017 |
| CN | 107037178 A | 8/2017 |
| EP | 3203079 A1 | 8/2017 |
| TW | M525446 U | 7/2016 |
| TW | M541542 U | 5/2017 |
| TW | M543870 U | 6/2017 |
| WO | WO 2012/154029 A1 | 11/2012 |
| WO | WO 2016/182437 A1 | 11/2016 |

OTHER PUBLICATIONS

Extended European Search Report for European Application No. 18184929.0, dated Oct. 24, 2018.

Lin et al., "Integrated Microfluidics/Electrochemical Sensor System for Monitoring of Environmental Exposures to Lead and Chlorophenols," Biomedical Microdevices, vol. 3, No. 4, Jan. 1, 2001, pp. 331-338.

Wu et al., "Modular Integration of Electronics and Microfluidic Systems Using Flexible Printed Circuit Boards," Lab Chip, vol. 10, 2010 (published online. Dec. 2, 2009), pp. 519-521.

* cited by examiner

ACTUATING AND SENSING MODULE

FIELD OF THE INVENTION

The present disclosure relates to an actuating and sensing module, and more particularly to an actuating and sensing module sensing gas by means of gas circulation.

BACKGROUND OF THE INVENTION

Nowadays, people pay much attention to monitoring environmental air quality in daily living, e.g., monitoring carbon monoxide, carbon dioxide, volatile organic compounds (VOC), PM2.5, and so on. The exposure of these substances in the environment can cause human health problems or can even harm the life. Therefore, it has become an important issue for every country to develop and implement environmental air quality monitoring technology.

However, the conventional gas detection equipment for example an air cleaning and filtering apparatus is bulky in volume and is not suitable to be carried by the user. Consequently, it is difficult for the user to obtain the real-time air quality information relating to the surrounding environment, and the user is still likely to be exposed to an environment with harmful gases. Therefore, an urgent problem that needs to be solved is how to obtain the gas quality information relating to the surrounding environment at anytime and anywhere.

However, since the conventional gas detection equipment fails to provide the waterproof and dustproof functions, some problems occur. If moisture or liquid is introduced into the equipment during the process of transferring the gas, the outputted gas tends to contain the moisture, so that the electronic components utilized to sense the gas is possibly damped, rusted or damaged. Moreover, the conventional gas detection equipment fails to provide dustproof function. If dust is introduced into the gas detection equipment during the process of transferring the gas, the components are possibly damaged and the gas transportation efficiency is reduced. Therefore, another urgent problem that needs to be solved is how to make the gas detection equipment has the waterproof and dustproof benefits.

Therefore, there is a need of providing an actuating and sensing module for allowing a gas detection apparatus or equipment to achieve small-size, miniature, silent, waterproof and dustproof benefits in order to eliminate the above drawbacks.

SUMMARY OF THE INVENTION

An object of the present disclosure provides an actuating and sensing module. While the gas fluctuation is generated by the high frequency operation of the piezoelectric membrane, a pressure gradient is generated in the designed flow channel and the gas flows at a high speed. Moreover, since there is an impedance difference between the feeding direction and the exiting direction, the gas can be transported from the inlet side to the outlet side. It benefits to solve the problems that the apparatus or equipment utilizing the conventional gas transportation device has a large volume, is difficult to be thinned, fails to achieve the purpose of portability, and has loud noises.

Another object of the present disclosure provides an actuating and sensing module with waterproof and dustproof functions. By being equipped with a protective film to filter the moisture and the dust, it benefits to solve the problems that while the moisture or the dust is introduced into the conventional gas transportation device during the process of transferring the gas, the components are possibly damaged and the gas transportation efficiency is reduced.

In accordance with an aspect of the present disclosure, an actuating and sensing module is provided. The actuating and sensing module includes a first substrate, a second substrate, at least one actuating device and at least one sensor. The first substrate includes at least one control circuit. The second substrate includes a gas inlet and a gas outlet. A gas flow channel is formed by stacking the second substrate on the first substrate. The gas inlet, the gas flow channel and the gas outlet are in communication with each other to define a gas flow loop. The at least one actuating device is disposed in the gas inlet of the second substrate and electrically connected to the at least one control circuit. The at least one sensor is disposed in the gas flow loop and electrically connected to the at least one control circuit. The actuating device is enabled to drive outside gas to flow into the gas flow channel through the gas inlet, and the gas flows through the at least one sensor and is discharged out through the gas outlet, so that the gas circulated in the gas flow loop is sensed by the at least one sensor.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
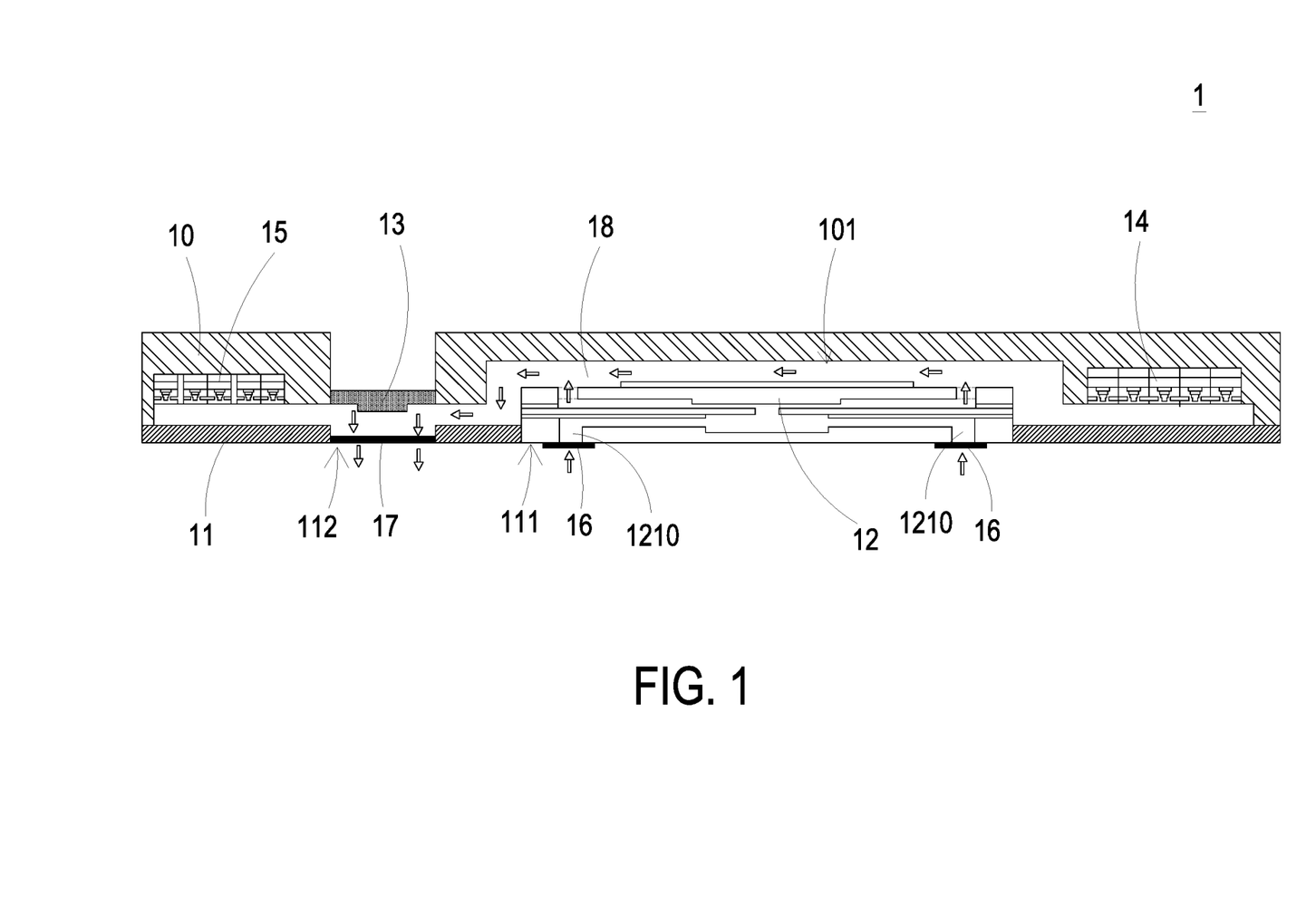
FIG. 1 is a cross-sectional view illustrating an actuating and sensing module according to a first embodiment of the present disclosure.

Please refer to FIG. 1. The present discourse provides an actuating and sensing module 1 including at least one first substrate 10, at least one control circuit 14, 15, at least one second substrate 11, at least one gas inlet 111, at least one gas outlet 112, at least one gas flow channel 18, at least one gas flow loop, at least one actuating device 12, at least one sensor 13 and at least one gas. The number of the first substrate 10, the second substrate 11, the gas inlet 111, the gas outlet 112, the gas flow channel 18, the gas flow loop and the gas is exemplified by one for each in the following embodiments but not limited thereto. It is noted that each of the first substrate 10, the second substrate 11, the gas inlet 111, the gas outlet 112, the gas flow channel 18, the gas flow loop and the gas can also be provided in plural numbers.

The present disclosure provides an actuating and sensing module, which is used to sense the air quality relating to the surrounding environment and has the waterproof, dustproof and silent benefits. The actuating and sensing module may be used in a mobile phone, a tablet, a wearable device or any similar portable electronic device constructed to contain CPU, RAM and other components. Please refer to FIG. 1, which is a cross-sectional view illustrating an actuating and sensing module according to a first embodiment of the present disclosure. As shown in the drawing, the actuating and sensing module 1 includes a first substrate 10, a second substrate 11, an actuating device 12 and a sensor 13. The first substrate 10 includes at least one control circuit. In the embodiment, the first substrate 10 includes a first control circuit 14 and a second control circuit 15. Both of the first control circuit 14 and the second control circuit 15 are an integrated circuit, respectively. Meanwhile, the first control circuit 14 is electrically connected to the actuating device 12, so as to provide a driving power. The second control circuit 15 is electrically connected to the sensor 13, so as to calculate and process the sensed data generated by the sensor 13. In other embodiments, the first substrate 10 includes a control circuit merely, and the single control circuit is electrically connected to the actuating device 12 and the sensor 13, so as to provide a driving power, calculate and process the sensed data generated by the sensor 13.

The second substrate 11 includes a gas inlet 111 and a gas outlet 112 running therethrough. The actuating device 12 is disposed in the gas inlet 111. While the first substrate 10 and the second substrate 11 are stacked together, a gas flow channel 18 is formed between the first substrate 10 and the second substrate 11. Moreover, the gas inlet 111, the gas flow channel 18 and the gas outlet 112 are in communication with each other, so as to form a gas flow loop. In the embodiment, the first substrate 10 further includes a recess 101. The gas flow channel 18 is formed between the recess 101 of the first substrate 10 and the second substrate 11, so as to achieve a structural design that is more space-saving. Meanwhile, the thickness of the overall structure of the actuating and sensing module 1 can be reduced, so as to achieve a thin and light volume.

In this embodiment, the first substrate 10 is a chip and can be for example but not limited to an application-specific integrated circuit (ASIC) chip or a system-on-chip (SOC) chip. The second substrate 11 is a chip cover plate and packaged on the first substrate 10. The recess 101 is formed on the first substrate 10 by a semiconductor process. The first control circuit 14 and the second control circuit 15 are packaged on the first substrate 10 by a semiconductor process. The gas inlet 111 and the gas outlet 112 are formed on the second substrate 11 by a semiconductor process. Moreover, the actuating device 12 is packaged on the gas inlet 111 of the second substrate 11 by a semiconductor process.

Please refer to FIG. 1 again. In the embodiment, the actuating device 12 is disposed to seal the gas inlet 111 of the second substrate 11, and electrically connected to the first control circuit 14, so as to obtain a driving power. The actuating device 12 is used for driving the gas to flow. The actuating device 12 includes a plurality of inlets 1210. With the actuating device 12 disposed to seal the gas inlet 111, the gas can be driven to flow into the gas inlet 111 though the inlets 1210 and transferred to the gas flow channel 18 in the actuating and sensing module 1. In the embodiment, the actuating device 12 is a resonant piezoelectric actuator gas pump. In other embodiments, the actuating device 12 can be one selected from the group consisting of a DC motor, an AC motor or a step motor with an electric actuating device, a magnetic coil motor with a magnetic actuating device, a heat pump with a thermal actuating device, a gas pump or a liquid pump with a fluid actuating device and a resonant piezoelectric actuator gas pump, but not limited thereto. The detailed structure of the actuating device 12 will be further described as follows.

Please refer to FIG. 1 again. The sensor 13 is disposed at any position of the gas flow loop, which is formed by sequentially communicating the gas inlet 111, the gas flow channel 18 and the gas outlet 112 with each other, so that the sensor 13 can be used for sensing a concentration of at least one target contained in the gas in the gas flow loop. In the embodiment, the sensor 13 is disposed on the first substrate 10 and aligned with the gas outlet 112 of the second substrate 11, but not limited thereto. In the embodiment, the sensor 13 is formed on the first substrate 10 by the semiconductor process and electrically connected to the second control circuit 15, so as to transmit the sensed data to the second control circuit 15. Consequently, the sensed data can be calculated and processed by the second control circuit 15. The sensor 13 can include at least one sensor selected from the group consisting of an oxygen sensor, a carbon monoxide sensor, a carbon dioxide sensor, a temperature sensor, an ozone sensor, a volatile organic compound sensor and a combination thereof, but not limited thereto. It can be varied according to the practical requirements.

In the embodiment, a pressure difference is generated by the actuating device 12. Consequently, the gas is inhaled into the gas flow channel 18 through the gas inlet 111 of the second substrate 11 from the outside of the actuating and sensing module 1, and transferred to the sensor 13. After flowing through the sensor 13, the gas is discharged out of the actuating and sensing module 1 through the gas outlet 112 of the second substrate 11. Thus, the sensor 13 can be utilized to monitor the concentration of at least one target contained in the ambient air, so as to obtain the real-time information relating to the monitoring of ambient air. At the same time, the speed of the gas circulation is accelerated by the actuating device 12, and the sensor 13 can obtain the most immediate information relating to the ambient air. That is, once it is detected that the surrounding environment contains toxic gases or dangerous gases, the user can be notified to take immediate protective measures to avoid the gas poisoning and the gas explosion.

Please refer to FIG. 1 again. The actuating and sensing module 1 further includes at least one first protective film 16 and at least one second protective film 17. The arrangement and the number of the first protective film 16 are corresponding to the arrangement and the number of the plural inlets 1210 of the actuating device 12, so as to cover the corresponding inlets 1210. The second protective film 17 is disposed to cover the gas outlet 112. In the other embodiments, the number of the first protective film 16 can be a single one, and the first protective film 16 is arranged to cover the gas inlet 111 of the second substrate 11. Since the first protective film 16 and the second protective film 17 are a waterproof, dustproof and gas-permeable film structure, the arrangement prevents moisture and dust from entering the gas flow channel 18 from the plurality of inlets 1210 or the gas inlet 111, and also prevents the moisture and dust from entering the gas flow channel 18 backward from the gas outlet 112. Thus, the inner space of the gas flow channel 18 can be maintained in a dry and dust-free situation. It is beneficial to prevent the components disposed inside the gas flow channel 18 from damage and rust caused by moisture or the accumulated dust.

In an embodiment, the first protective film 16 and the second protective film 17 comply with the Rating IP64 of International Protection Marking (IEC 60529), i.e., Dust protection level 6 (Complete protection, No ingress of dust) and Water protection level 4 (Protection against Splashing of water: Water splashing against the enclosure from any direction shall have no harmful effect). In another embodiment, the first protective film 16 and the second protective film 17 comply with the Rating IP68 of International Protection Marking (IEC 60529), i.e., Dust protection level 6 and Water protection level 8 (Continuous immersion in water produces no harmful effects). In other embodiments, the first protective film 16 and the second protective film 17 comply with the Rating IP65, IP66 or IP67 of International Protection Marking (IEC 60529), but not limited thereto.

Figure 2A:
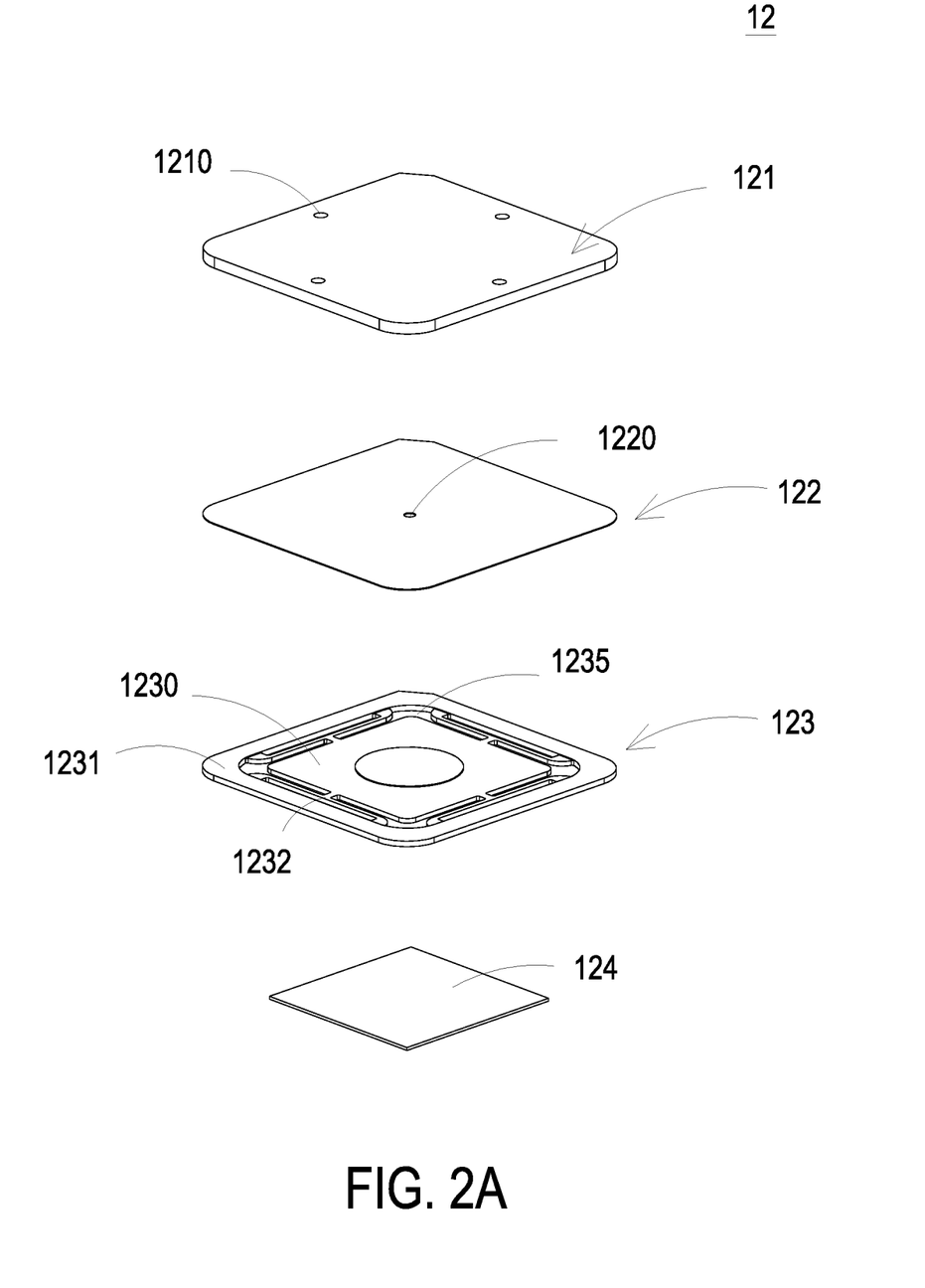
FIG. 2A is a schematic exploded view illustrating the actuating and sensing module according to the first embodiment of the present disclosure and taken along a first viewpoint.
Figure 2B:
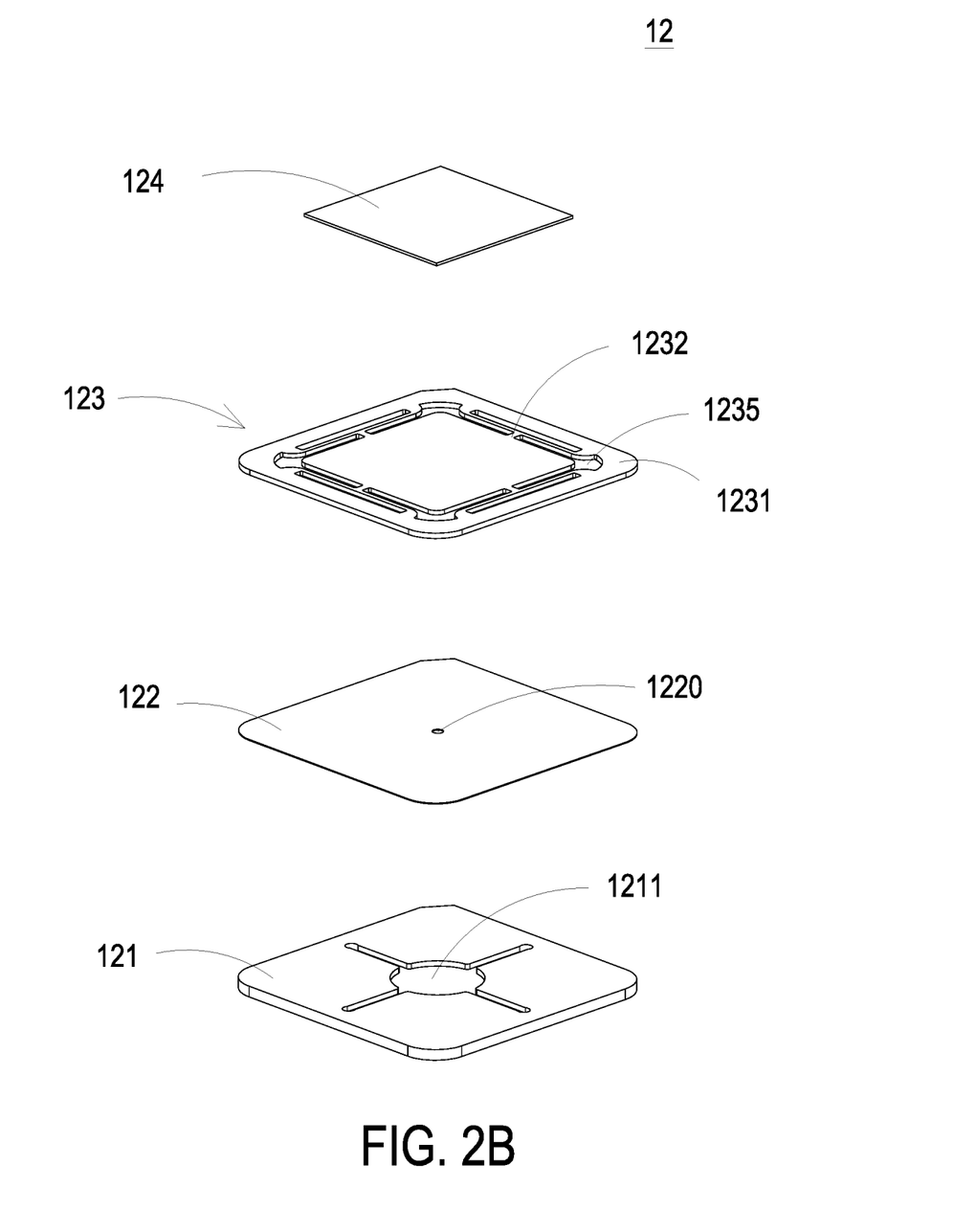
FIG. 2B is a schematic exploded view illustrating the actuating and sensing module according to the first embodiment of the present disclosure and taken along a second viewpoint.

Please refer to FIGS. 2A and 2B. FIG. 2A is a schematic exploded view illustrating the actuating and sensing module according to the first embodiment of the present disclosure and taken along a first viewpoint. FIG. 2B is a schematic exploded view illustrating the actuating and sensing module according to the first embodiment of the present disclosure and taken along a second viewpoint. In the embodiment, the actuating device 12 is a resonant piezoelectric actuator gas pump. For describing and emphasizing the features of the structure, the structure of the actuating device 12 is decomposed, but not intended to illustrate that it is a detachable structure. As shown in the drawings, in the embodiment, the actuating device 12 includes an inlet plate 121, a resonance membrane 122, an actuating membrane 123 and a piezoelectric membrane 124. The inlet plate 121, the resonance membrane 122, the actuating membrane 123 and the piezoelectric membrane 124 are stacked on each other sequentially to be assembled as the actuating device 12. A compressing chamber 1221 (shown in FIG. 4A) is formed between the resonance membrane 122 and the actuating membrane 123, but not limited thereto. It can be varied according to the practical requirements.

Please refer to FIGS. 2A and 2B. In the embodiment, the plural inlets 1210 are disposed on the inlet plate 121. In the embodiment, the number of the inlets 1210 is exemplified by four but not limited thereto. The number of the inlets 1210 can be arbitrarily varied according to the practical requirements. In response to the action of the atmospheric pressure, the gas can be inhaled into the actuating device 12 through the inlets 1210 from the outside of the actuating device 12. In the embodiment, the inlet plate 121 further includes a convergence chamber 1211 (shown in FIG. 2B) and the convergence chamber 1211 is in communication with the plural inlets 1210. In that, the gas is inhaled through the inlets 1210, transferred and converged to the convergence chamber 1211 for temporarily storing the gas and transferring the gas. The resonance membrane 122 includes a central aperture 1220 corresponding to the convergence chamber 1211 disposed on the bottom surface of the inlet plate 121, so as to transfer the gas to the compressing chamber 1221 (shown in FIG. 4A).

Figure 3A:
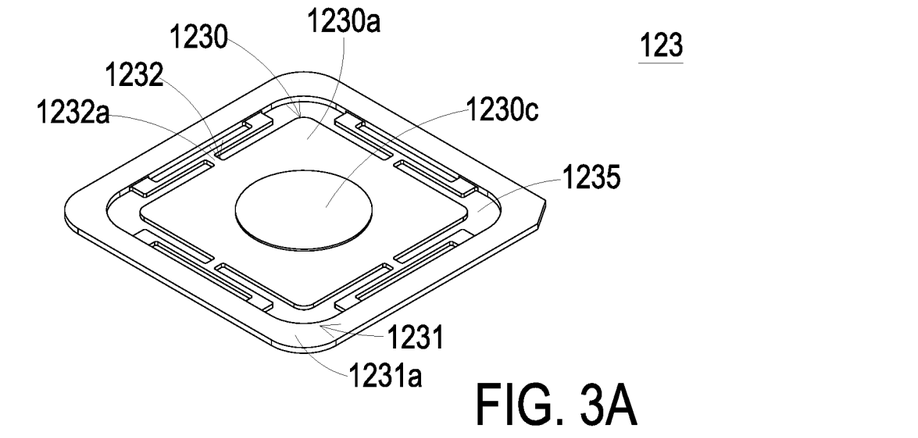
FIG. 3A is a schematic perspective view illustrating the actuating membrane of the actuating and sensing module of FIG. 2A and taken along the front side.
Figure 3B:
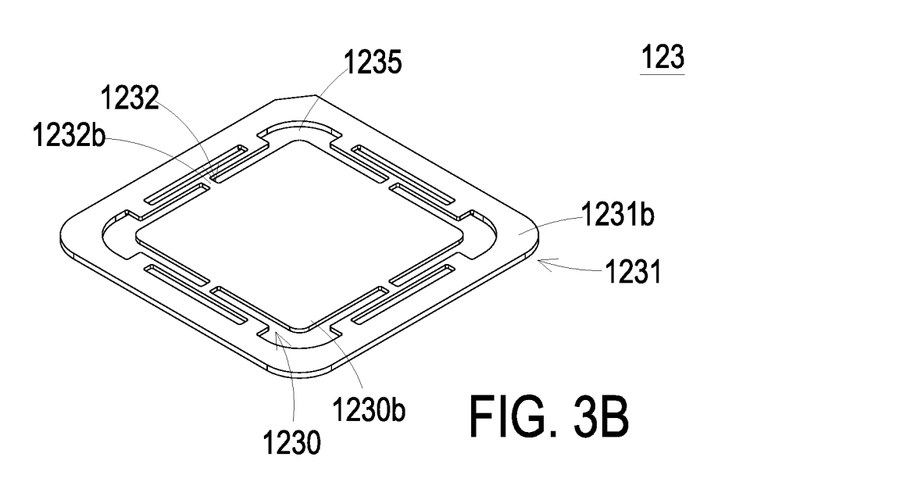
FIG. 3B is a schematic perspective view illustrating the actuating membrane of the actuating and sensing module of FIG. 2A and taken along the rear side.
Figure 3C:
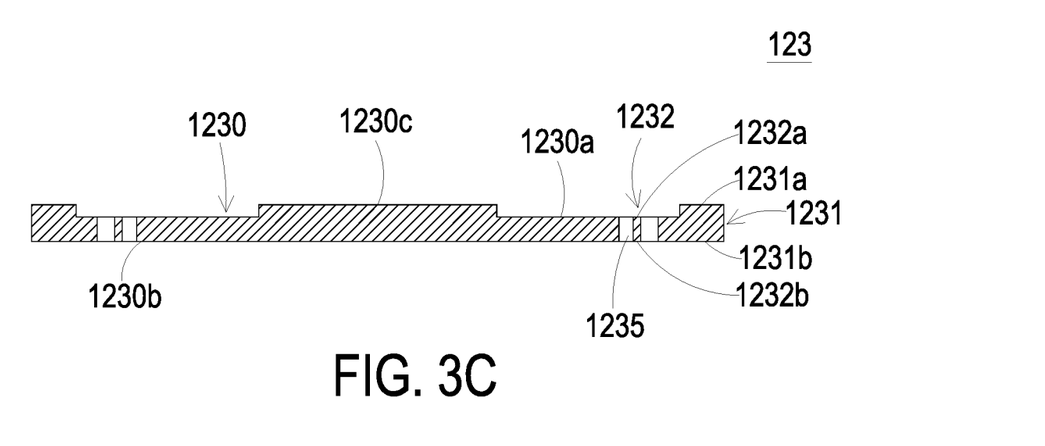
FIG. 3C is a schematic cross-sectional view illustrating the actuating membrane of the actuating and sensing module of FIG. 2A.

Please refer to FIGS. 2A to 3C. FIG. 3A is a schematic perspective view illustrating the actuating membrane of the actuating and sensing module of FIG. 2A and taken along the front side. FIG. 3B is a schematic perspective view illustrating the actuating membrane of the actuating and sensing module of FIG. 2A and taken along the rear side. FIG. 3C is a schematic cross-sectional view illustrating the actuating membrane of the actuating and sensing module of FIG. 2A. As shown in the drawings, in the embodiment, the actuating membrane 123 further includes a suspension part 1230, an outer frame 1231 and a plurality of connection parts 1232. The plurality of connection parts 1232 are connected between the suspension part 1230 and the outer frame 1231, while an end of each connection part 1232 is connected with the outer frame 1231 and another end of each connection part 1232 is connected with the suspension part 1230. Moreover, a plurality of vacant spaces 1235 are formed among the connection parts 1232, the suspension part 1230 and the outer frame 1231 for allowing the gas to go through. The arrangement, the type and the number of the suspension part 1230, the outer frame 1231 and the connection parts 1232 are not restricted and can be varied according to the practical requirements.

In the embodiment, the suspension part 1230 is a stepped structure. Namely, the suspension part 1230 includes a bulge 1230*c* disposed on the top surface 1230*a* of the suspension part 1230. The bulge 1230*c* can be but not limited to a circular convex structure. As shown in FIGS. 3A to 3C, a top surface of the bulge 1230*c* of the suspension part 1230 is coplanar with a top surface 1231*a* of the outer frame 1231, while the top surface 1230*a* of the suspension part 1230 is coplanar with a top surface 1232*a* of the connection parts 1232. Moreover, there is a specified depth from the top surface of the bulge 1230*c* of the suspension part 1230 and the top surface 1231*a* of the outer frame 1231 to the top surface 1230*a* of the suspension part 1230 and the top surface 1232*a* of the connection parts 1232. As shown in FIGS. 3A and 3C, a bottom surface 1230*b* of the suspension part 1230, a bottom surface 1231*b* of the outer frame 1231 and a bottom surface 1232*b* of the connection parts 1232 are coplanar with each other and form a flat plane, but not limited thereto.

Please refer to FIGS. 2A and 2B again. The piezoelectric membrane 124 is attached on the bottom surface 1230*b* of the suspension part 1230 of the actuating membrane 123, so that the actuating membrane 123 is enabled to vibrate along a vertical direction in a reciprocating manner and drive the resonance membrane 122 to vibrate. Thus, the pressure of the compressing chamber 1221 between the resonance membrane 122 and actuating membrane 123 is varied to transport the gas.

In the embodiment, when the piezoelectric membrane 124 is enabled to drive the actuating membrane 123, the gas is inhaled into the convergence chamber 1211 through the plural inlets 1210 of the inlet plate 121 and transferred to the compressing chamber 1221 through the central aperture 1220 of the resonance membrane 122 and flows out from the vacant space 1235 of the actuating membrane 123, so that the gas is introduced into the gas flow channel 18.

Figure 4A:
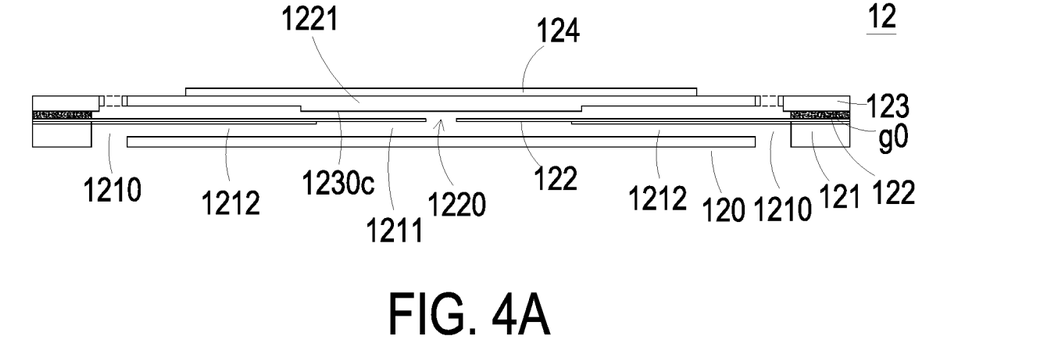
FIGS. 4A to 4E schematically illustrate the actions of the actuating and sensing module of FIG. 2B.
Figure 4B:
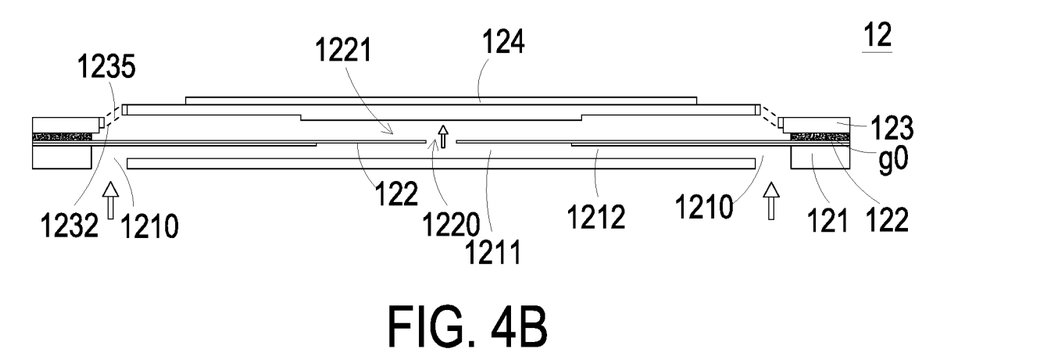

Please refer to FIGS. 2A, 2B and 4A to 4E. FIGS. 4A to 4E schematically illustrate the actions of the actuating and sensing module of FIG. 2B. Firstly, as shown in FIG. 4A, the actuating device 12 is formed by stacking the inlet plate 121, the resonance membrane 122, the actuating membrane 123 and the piezoelectric membrane 124 on each other sequentially. A spacer g0, which can be for example an adhesive layer, is formed between the resonance membrane 122 and the actuating membrane 123, so that a depth of the spacer g0 can be maintained between the resonance membrane 122 and the bulge 1230*c* of the suspension part 1230 of the piezoelectric membrane 123. Thus, the gas can be transferred quickly, the contact interference is reduced and the generated noise is largely reduced. In some embodiments, alternatively, the height of the outer frame 1231 of the actuating membrane 123 is increased, so that the spacer g0 is formed and a gap is added while the actuating membrane 123 is assembled with the resonance membrane 122, but not limited thereto.

Please refer to FIGS. 4A to 4E. As shown in the drawings, a chamber for converging the gas is defined collaboratively by the central aperture 1220 of the resonance membrane 122 and the convergence chamber 1211 of the inlet plate 121. The compressing chamber 1221 is defined collaboratively be the resonance membrane 122 and the actuating membrane 123 for temporarily storing the gas. Through the central aperture 1220 of the resonance membrane 122, the compressing chamber 1221 is in communication with the convergence chamber 1211 of the inlet plate 121. The peripheral regions of the compressing chamber 1221 are in communication with the air flow channel 18 (shown in FIG. 1) arranged on the compressing chamber 1221 through the vacant space 1235 between the connection parts 1232 of the actuating membrane 123.

Figure 4C:
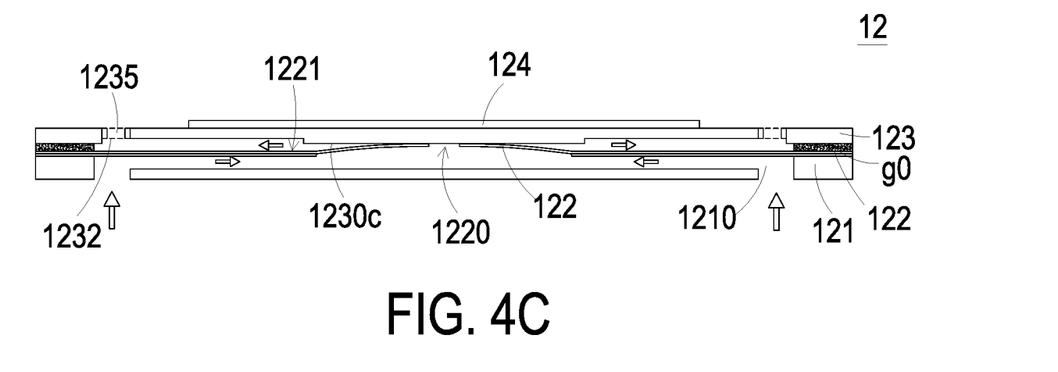
Figure 4D:
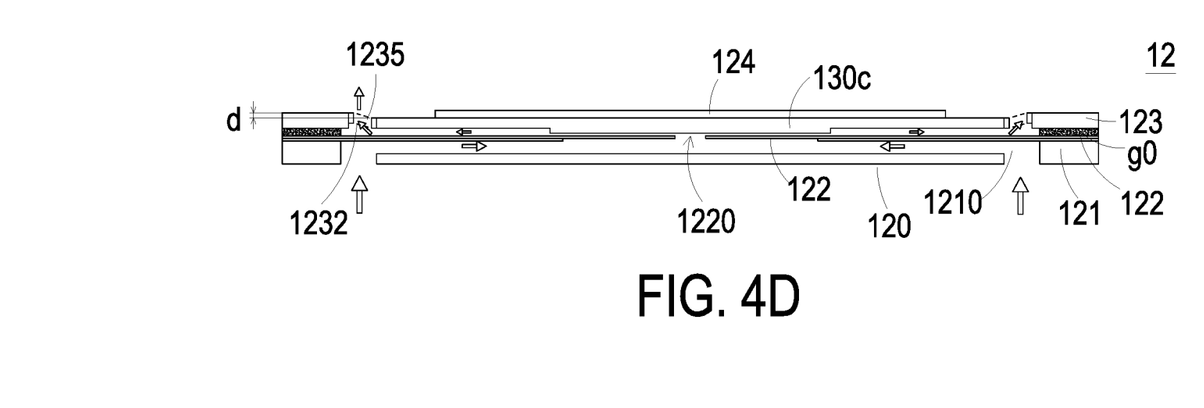
Figure 4E:
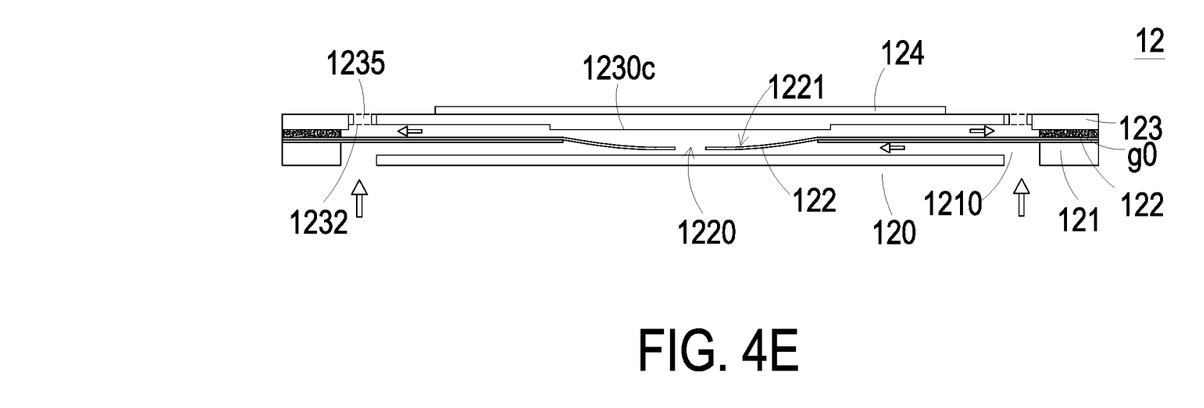

When the actuating device 12 is enabled, the actuating membrane 123 vibrates along a vertical direction in a reciprocating manner by using the connection parts 1232 as a fulcrum. Please refer to FIG. 4B, when the actuating membrane 123 vibrates along a first direction in response to the applied voltage, the gas is inhaled through the plural inlets 1210 of the inlet plate 121 and converged into the convergence chamber 1211. Meanwhile, the gas is further transferred along the first direction into the compressing chamber 1221 through the central aperture 1220 of the resonance membrane 122. Afterward, as the actuating membrane 123 is enabled to drive the resonance membrane 122, the resonance of the resonance membrane 122 occurs. Consequently, the resonance membrane 122 vibrates along the vertical direction in the reciprocating manner. As shown in FIG. 4C, the resonance membrane 122 moves along the first direction to contact and attach on the bulge 1230*c* of the suspension part 1230 of the actuating membrane 123. Owing to the deformation of the resonance membrane 122 described above, a middle communication space of the compressing chamber 1221 is closed, and the volume of the compressing chamber 1221 is shrunk. Under this circumstance, the gas in the compressing chamber 1221 is pushed toward peripheral regions of the compressing chamber 1221 and flows along the first direction through the vacant space 1235 between the connection parts 1232 of the actuating membrane 123. As shown in FIG. 4D, the resonance membrane 122 has returned to its original position. The actuating membrane 123 vibrates along a second direction in response to the applied voltage. Consequently, the volume of the compressing chamber 1221 is continuously shrunk and the actuating membrane 123 vibrates along the second direction with a second direction displacement d, which makes the gas in the compressing chamber 1221 continuously pushed toward peripheral regions. Meanwhile, the gas is continuously transferred to be filtered through the first protective film 16 and the second protective film 17 (shown in FIG. 1) and inhaled into the convergence chamber 1211 from the inlets 1210 of the inlet plate 121. As shown in FIG. 4E, the resonance membrane 122 moves along the second direction, which is caused by the resonance of the second direction motion of the actuating membrane 123. Consequently, the gas is transferred from the convergence chamber 1211 into the compressing chamber 1221 through the central aperture 1220, transferred through the vacant space 1235 among the connection parts 1232 of the actuating membrane 123, and further transferred along the first direction to flow out of the actuating device 12. In this way, a pressure gradient is generated in the gas flow loop of the actuating device 12 to facilitate the gas to flow at a high speed. Moreover, since there is an impedance difference between the feeding direction and the exiting direction, the gas can be transported from the inlet side to the outlet side. Even if a gas pressure exists at the outlet side, the actuating device 12 still has the capability of pushing the gas to the outlet side while achieving the silent efficacy. In some embodiments, the vibration frequency of the resonance membrane 122 along the vertical direction in the reciprocating manner is identical to the vibration frequency of the actuating membrane 123. That is, the resonance membrane 122 and the actuating membrane 123 are synchronously vibrated along the first direction or the second direction. It is noted that numerous modifications and alterations of the actions of the actuating device 12 may be made while retaining the teachings of the disclosure.

In another embodiment, the actuating device 12 can be a microelectromechanical system (MEMS) gas pump, and the surface of the material is micro-machined by means of dry and wet etching, so as to make an integrally formed miniature gas pump. The resonance membrane 122 includes a flexible suspension structure made by a surface micromachining process. The actuating membrane 123 includes a hollow and suspension structure made by the surface micromachining process. The material of the actuating membrane 121 can be a metallic membrane or a polysilicon membrane. The piezoelectric membrane 124 can be a metal oxide membrane made by a sol-gel process. The present disclosure is not limited thereto.

From the above descriptions, the present disclosure provides the actuating and sensing module. After the gas is transferred through the first and second protective films, the moisture and dust contained in the gas are removed by the protective films. After the gas is filtered, the gas is fed into the actuating and sensing module through the inlets. When the actuating membrane is activated by the piezoelectric membrane, a pressure gradient is generated in the designed flow channels and the designed chambers for allowing the gas to be transported to the gas flow channel at a high speed. The gas is further discharged out of the gas flow channel through the gas outlet. Under this circumstance, the gas flow loop is achieved, and the gas can be quickly transferred while achieving silent efficacy. With the sensor for sensing the gas, the most immediate information relating to the ambient air can be obtained at anytime and anywhere. In addition, due to the arrangement of the first protective film and the second protective film, it prevents the inner components from damage and rust caused by moisture or accumulated dust. Consequently, the gas transportation efficiency is enhanced and the performance of the device with the actuating and sensing module is enhanced. Therefore, the actuating and sensing module of the present disclosure is industrially valuable.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating and sensing module, comprising:
   a first substrate comprising a first control circuit and a second control circuit;
   a second substrate comprising a gas inlet and a gas outlet, wherein a gas flow channel is formed by stacking the second substrate with the first substrate, wherein the gas inlet, the gas flow channel and the gas outlet are in communication with each other to define a gas flow loop;
   at least one actuating device disposed in the gas inlet of the second substrate and electrically connected to the first control circuit so as to obtain a driving power; and
   at least one sensor disposed in the gas flow loop and electrically connected to the second control circuit so as to transmit a sensed data to the second control circuit to be calculated and processed;
   wherein the sensed data is generated by the at least one sensor, wherein the at least one actuating device is enabled to drive outside gas to flow into the gas flow channel through the gas inlet, and the gas flows through the at least one sensor and is discharged out through the gas outlet, so that the gas circulated in the gas flow loop is sensed by the at least one sensor.

2. The actuating and sensing module according to claim 1, wherein the at least one sensor is disposed on the first substrate and aligned with the gas outlet.

3. The actuating and sensing module according to claim 1, wherein the first substrate comprises a recess, and the recess is defined as the gas flow channel between the first substrate and the second substrate while the first substrate and the second substrate are stacked with each other.

4. The actuating and sensing module according to claim 1, wherein the at least one sensor includes at least one selected from the group consisting of an oxygen sensor, a carbon monoxide sensor, a carbon dioxide sensor, a temperature sensor, an ozone sensor, a volatile organic compound sensor and a combination thereof.

5. The actuating and sensing module according to claim 1, wherein the at least one actuating device includes one selected from the group consisting of a DC motor, an AC motor or a step motor with an electric actuating device, a magnetic coil motor with a magnetic actuating device, a heat pump with a thermal actuating device, a gas pump or a liquid pump with a fluid actuating device and a resonant piezoelectric actuator gas pump.

6. The actuating and sensing module according to claim 1, wherein the at least one actuating device is a microelectromechanical system gas pump and the microelectromechanical system gas pump comprises:
   an inlet plate comprising at least one inlet and a convergence chamber;
   a resonance membrane including a suspension structure made by a surface micromachining process and comprising a central aperture;
   an actuating membrane including a hollow and suspension structure made by the surface micromachining process and comprising a suspension part, an outer frame and at least one connection part, wherein at least one vacant space is defined among the at least one connection part, the suspension part and the outer frame; and
   a piezoelectric membrane attached on a surface of the suspension part,
   wherein the inlet plate, the resonance membrane and the actuating membrane are stacked sequentially and a compressing chamber is formed between the resonance membrane and the actuating membrane, wherein while the piezoelectric membrane is enabled to drive the actuating membrane, the gas is inhaled through the at least one inlet, transferred and converged to the convergence chamber, transferred to the compressing chamber through the central aperture of the resonance membrane and discharged out through the at least one vacant space, so that the gas is introduced in the gas flow channel.

7. The actuating and sensing module according to claim 6, wherein the actuating membrane includes one of a metallic membrane and a polysilicon membrane.

8. The actuating and sensing module according to claim 6, wherein the piezoelectric membrane includes a metal oxide membrane made by a sol-gel process.

9. The actuating and sensing module according to claim 6, wherein the microelectromechanical system gas pump is an integrally formed structure.

10. The actuating and sensing module according to claim 6, further comprising at least one first protective film and at least one second protective film, wherein the at least one first protective film is disposed to cover one of the at least one inlet and the gas inlet, and the at least one second protective film is disposed to cover the gas outlet, wherein the at least one first protective film and the at least one second protective film include a waterproof, dustproof and gas-allowed film structure, respectively.

11. The actuating and sensing module according to claim 1, wherein the at least one actuating device is a resonant piezoelectric actuator gas pump and the resonant piezoelectric actuator gas pump comprises:
   an inlet plate comprising at least one inlet and a convergence chamber;
   a resonance membrane including a suspension structure and comprising a central aperture;
   an actuating membrane including a hollow and suspension structure and comprising a suspension part, an outer frame and at least one connection part, wherein at least one vacant space is defined among the at least one connection part, the suspension part and the outer frame; and
   a piezoelectric membrane attached on a surface of the suspension part,
   wherein the inlet plate, the resonance membrane and the actuating membrane are stacked sequentially and a compressing chamber is formed between the resonance membrane and the actuating membrane, wherein while the piezoelectric membrane is enabled to drive the actuating membrane, the gas is inhaled through the at least one inlet, transferred and converged to the convergence chamber, transferred to the compressing chamber through the central aperture of the resonance membrane and discharged out through the at least one vacant space, so that the gas is introduced in the gas flow channel.

12. The actuating and sensing module according to claim 11, further comprising at least one first protective film and at least one second protective film, wherein the at least one first protective film is disposed to cover one of the at least one inlet and the gas inlet, and the at least one second protective film is disposed to cover the gas outlet, wherein the at least one first protective film and the at least one second protective film include a waterproof, dustproof and gas-permeable film structure, respectively.

13. The actuating and sensing module according to claim 12, wherein the at least one first protective film and the at least one second protective film comply with Rating IP64 of International Protection Marking (IEC 60529).

14. The actuating and sensing module according to claim 12, wherein the at least one first protective film and the at least one second protective film comply with Rating IP65 of International Protection Marking (IEC 60529).

15. The actuating and sensing module according to claim 12, wherein the at least one first protective film and the at least one second protective film comply with Rating IP66 of International Protection Marking (IEC 60529).

16. The actuating and sensing module according to claim 12, wherein the at least one first protective film and the at least one second protective film comply with Rating IP67 of International Protection Marking (IEC 60529).

17. The actuating and sensing module according to claim 12, wherein the at least one first protective film and the at least one second protective film comply with Rating IP68 of International Protection Marking (IEC 60529).

18. An actuating and sensing module, comprising:
- at least one first substrate comprising a first control circuit and a second control circuit;
- at least one second substrate comprising at least one gas inlet and at least one gas outlet, wherein at least one gas flow channel is formed by stacking the at least one second substrate on the at least one first substrate, wherein the at least one gas inlet, the at least one gas flow channel and the at least one gas outlet are in communication with each other to define at least one gas flow loop;
- at least one actuating device disposed in the at least one gas inlet of the at least one second substrate and electrically connected to the first control circuit so as to obtain a driving power; and
- at least one sensor disposed in the at least one gas flow loop and electrically connected to the second control circuit so as to transmit a sensed data to the second control circuit to be calculated and processed;
- wherein the sensed data is generated by the at least one sensor, wherein the at least one actuating device is enabled to drive at least one outside gas to flow into the at least one gas flow channel through the at least one gas inlet, and the at least one gas flows through the at least one sensor and is discharged out through the at least one gas outlet, so that the at least one gas circulated in the at least one gas flow loop is sensed by the at least one sensor.

\* \* \* \* \*